(12) United States Patent
Adlerstein et al.

(10) Patent No.: US 8,329,405 B2
(45) Date of Patent: Dec. 11, 2012

(54) METHOD FOR DETECTION OF MUTANT ALLELES COMBINING REAL TIME PCR AND REMS-PCR

(75) Inventors: Daniel Adlerstein, Arese (IT); Eriet Shehi, Bollate (IT); Giulia Amicarelli, Carnate (IT)

(73) Assignee: Diasorin S.p.A., Saluggia (VC) (IT)

( * ) Notice: Subject to any disclaimer, the term of this patent is extended or adjusted under 35 U.S.C. 154(b) by 559 days.

(21) Appl. No.: 12/443,175

(22) PCT Filed: Sep. 24, 2007

(86) PCT No.: PCT/EP2007/060116
§ 371 (c)(1),
(2), (4) Date: Apr. 1, 2010

(87) PCT Pub. No.: WO2008/037694
PCT Pub. Date: Apr. 3, 2008

(65) Prior Publication Data
US 2010/0190157 A1    Jul. 29, 2010

(30) Foreign Application Priority Data
Sep. 26, 2006    (EP) .................................... 06020128

(51) Int. Cl.
*C12P 19/34*    (2006.01)
(52) U.S. Cl. ...................................... 435/6.12; 435/91.2
(58) Field of Classification Search ................. 435/6.12, 435/91.2
See application file for complete search history.

(56) References Cited

U.S. PATENT DOCUMENTS

2003/0165898 A1* 9/2003 Todd ................................. 435/6
2006/0188902 A1* 8/2006 Narayanan et al. ............... 435/6

FOREIGN PATENT DOCUMENTS

WO           01/49877 A    7/2001
WO       2006/074222 A    7/2006

OTHER PUBLICATIONS

Roberts et al., BioTechniques 27(3), 418, 420, 422 (1999).*
Amicarelli et al., Clinical Chemistry 52(10), 1855-1863 (2006).*
Amicarelli, Giulia, et al: "Genotype-specific signal generation based on digestion of 3-way DNA junctions: Applicati on to KRAS variation detection", Clinical Chemistry, vol. 52, No. 10, Aug. 17, 2006, pp. 1855-1863, Online publication Aug. 17, 2006.

(Continued)

*Primary Examiner* — Kenneth R. Horlick
(74) *Attorney, Agent, or Firm* — Lucas & Mercanti, LLP

(57) ABSTRACT

The invention provides an amplification system for the simultaneous detection of mutant alleles, and identification of the specific mutated sequence. A sample is enriched and simultaneously genotyped by the presence of peptide nucleic acids (PNAs) probes in an homogeneous single tube amplification reaction, by detecting the cleavage of a fluorophore quencher from the 5'-end of PCR products and, concurrently, selecting DNA that includes specific mutations relative to wild type, by employing a thermostable endonuclease that will only cleave an amplicon formed on a mutation bearing template strand. Oligonucleotides and kits for conducting the amplification system are also provided.

24 Claims, 13 Drawing Sheets

OTHER PUBLICATIONS

Figure 1:
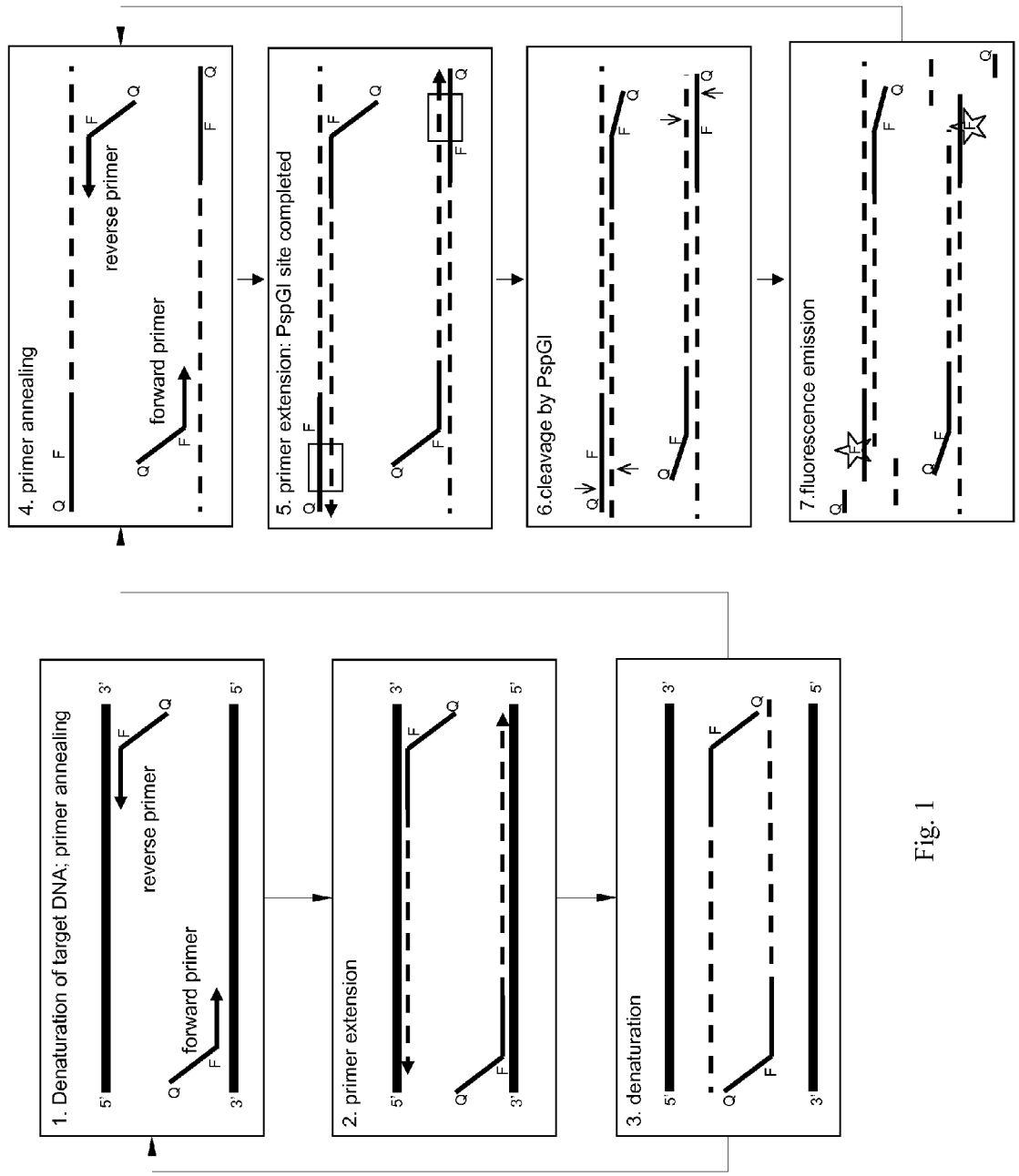

Ghezzi, E., et al: "Evaluation of OCEAN a new restriction endonuclease-based amplification reaction for SNP genotyping", Clinical Chemistry, vol. 51, No. Suppl. 6, 2005, p. A186, & Annual Meeting of the American-Association-For-Clinical-Chemistry; Orlando, FL, USA; Jul. 24-28, 2005.

Hruban, R. H., et al: "K-RAS oncologene activation in adenocarcinoma of the human pancreas. A study of 82 carcinomas using a combination of mutant-enriched polymerase chain reaction analysis and allele-specific oligonucleotide hybridization", American Journal of Pathology, Philadelphia, PA, US, vol. 143, No. 2, Aug. 1, 1993, pp. 545-554.

Roberts, N. J., et al: "Rapid, sensitive detection of mutant alleles in codon of 12 of K-RAS by rems-PCR", Biotechniques, Informa Life Sciences Publishing, Westborough, MA, US, vol. 27, No. 3, Sep. 1999, p. 418,420,422.

Todd, Alison V., et al: "DzyNA-PCR: Use of DNAzymes to detect and quantify nucleic acid sequences in a real time fluorescent format", Clinical Chemistry, American Association for Clinical Chemistry, Washington, DC, US, vol. 46, No. 5, May 2000, pp. 625-630.

Dabritz, J., et al: "Detection of Ki-ras mutations in tissue and plasma samples of patients with pancreatic cancer using PNA-mediated PCR clamping and hybridisation probes", British Journal of Cancer Jan. 31, 2005, vol. 92, No. 2, pp. 405-412.

* cited by examiner

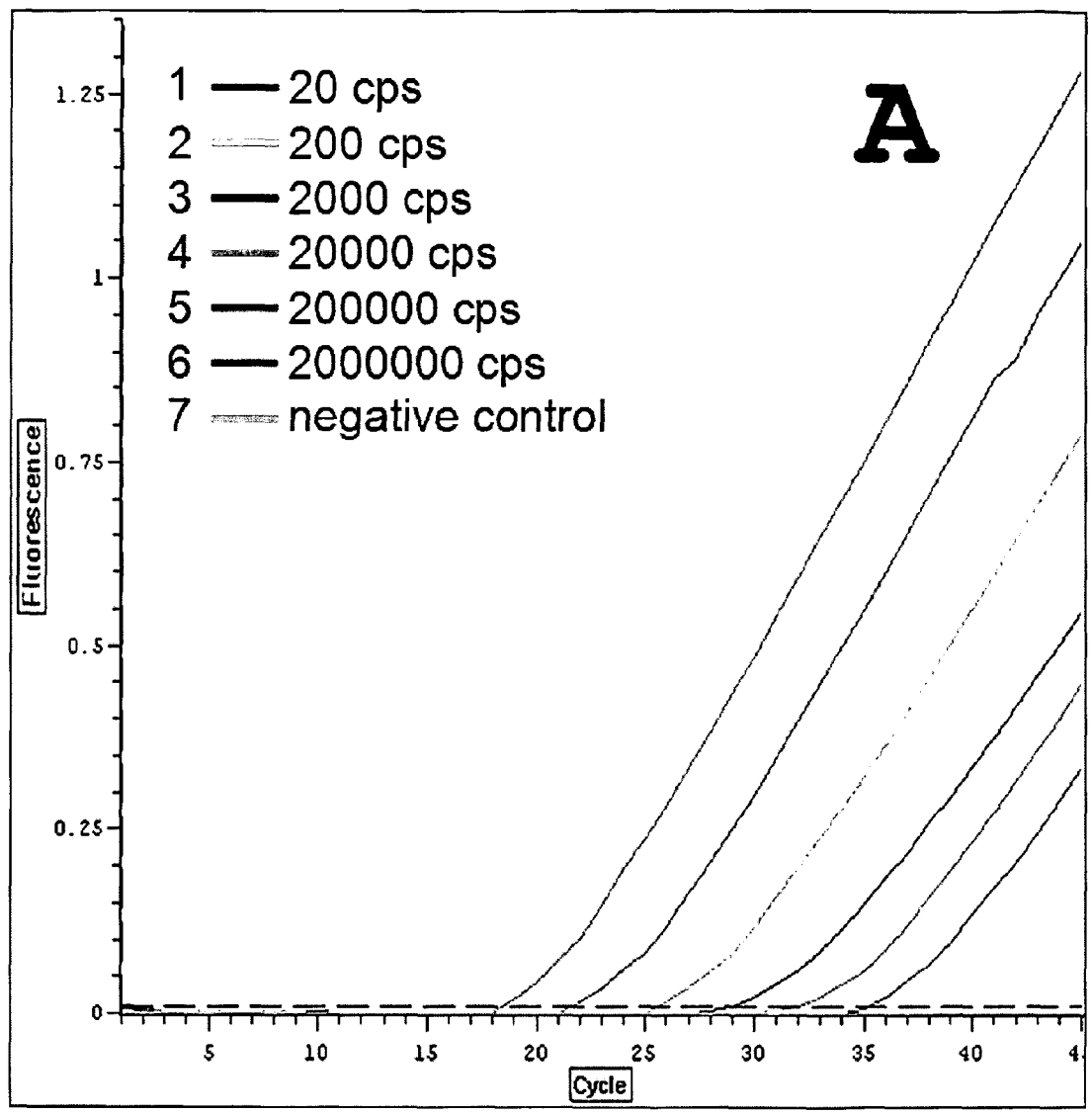
Fig. 4 (1/3)

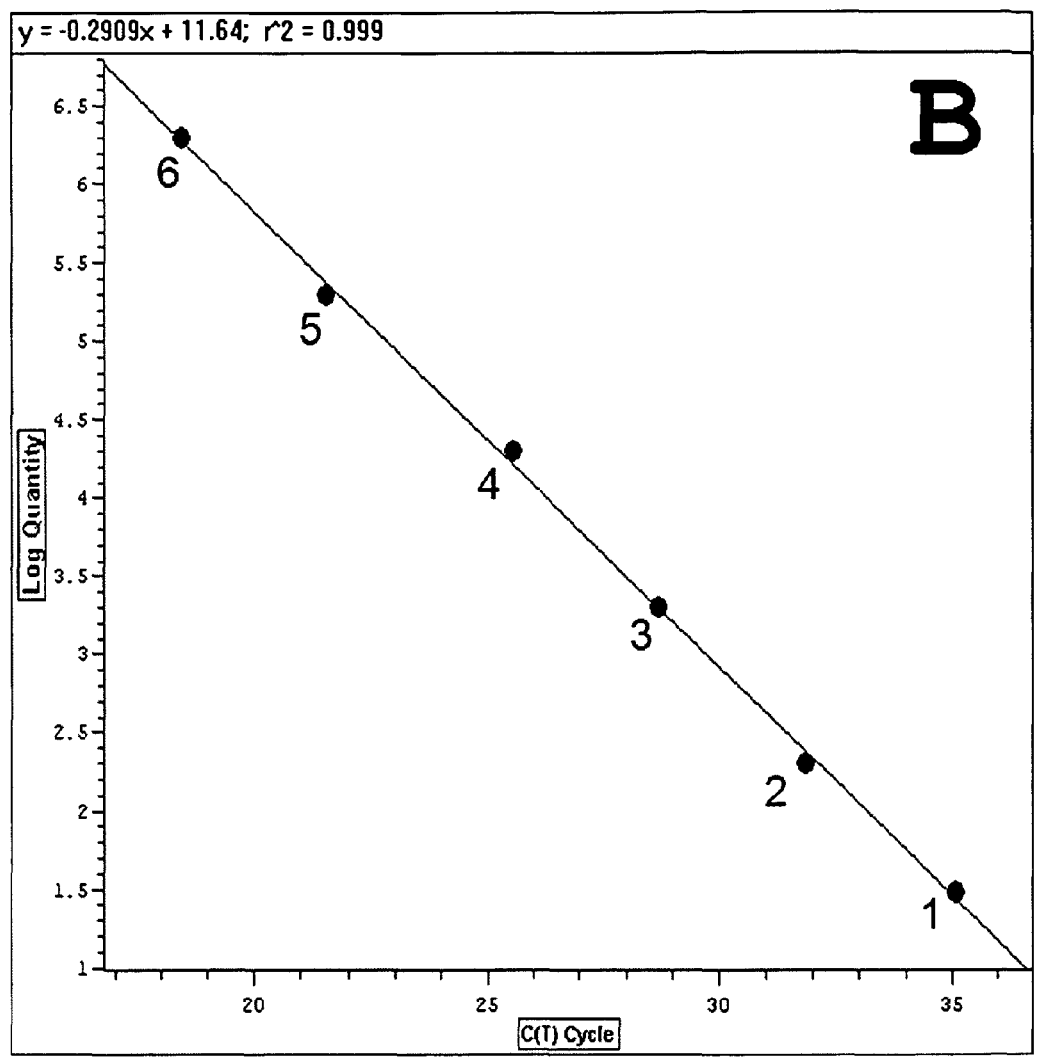
Fig. 4 (2/3)

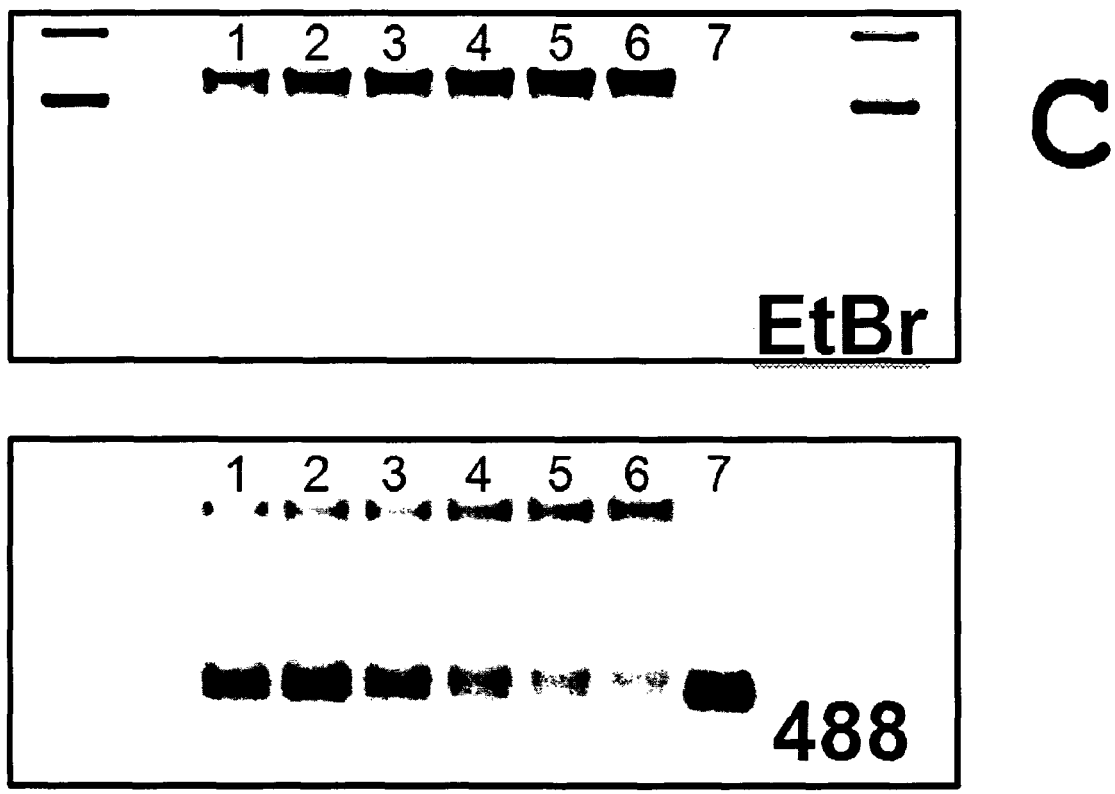
Fig. 4 (3/3)

METHOD FOR DETECTION OF MUTANT ALLELES COMBINING REAL TIME PCR AND REMS-PCR

INTRODUCTION

Somatic mutations are useful markers for early detection of cancer (1, 2). For example, the Kras (v-Ki-ras2 Kirsten rat sarcoma viral oncogene homo log) mutation in codon 12 occurs in different kinds of tumors, such as pancreatic adenocarcinoma, lung cancer and colorectal cancer (3-14).

Below is the Kras sequence (exon 1 region) from Genebank accession number AF285779, McKinzie and Parsons, Mutation Research 517, 209-220, 2002), Codon 12 sequence of interest is underlined:

```
                                              (SEQ ID No. 9)
ACTAGGAAAACTGTAACAATAAGAGTGGAGATAGCTGTCAGCAACTTTTG

TGAGGGTGTGCTACAGGGTGTAGAGCACTGTGAAGTCTCTACATGAGTGA

AGTCATGATATGATCCTTTGAGAGCCTTTAGCCGCCGCAGAACAGCAGTC

TGGCTATTTAGATAGAACAACTTGATTTTAAGATAAAAGAACTGTCTATG

TAGCATTTATGCATTTTTCTTAAGCGTCGATGGAGGAGTTTGTAAATGAA

GTACAGTTCATTACGATACACGTCTGCAGTCAACTGGAATTTTCATGATT

GAATTTTGTAAGGTATTTTGAAATAATTTTTCATATAAAGGTGAGTTTGT

ATTAAAAGGTACTGGTGGAGTATTTGATAGTGTATTAACCTTATGTGTGA

CATGTTCTAATATAGTCACATTTTCATTATTTTTATTATAAGGCCTGCTG

AAAATGACTGAATATAAACTTGTGGTAGTTGGAGCTGGTGGCGTAGGCAA

GAGTGCCTTGACGATACAGCTAATTCAGAATCATTTTGTGGACGAATATG

ATCCAACAATAGAGGTAAATCTTGTTTTAATATGCATATTACTGGTGCAG

GACCATTCTTTGATACAGATAAAGGTTTCTCTGACCATTTTCATGAGT.
```

The detection of gene alterations of the Kras type can represent a useful tool for early diagnosis of neoplasia in clinical samples. Detecting such mutations for population screening purposes, presents a difficulty due to the large excess of wild type DNA usually found in clinical specimens. This excess of wild type DNA can exhaust essential reagents, masking the mutant signal during the detection step of the assay. For these reasons, the common technologies used in this field present a preliminary step of suppression of the wild type allele (PCR-clamping (15)) or enrichment of the mutant allele during amplification (Restriction endonuclease-mediated selective polymerase chain reaction, REMS-PCR (16)), followed by a detection step for revealing the mutant signal. Most of these methods are not convenient for use in clinical practice because the multi-step procedure increases the risk of contaminations and false positive results.

The authors of the invention were able to set up a novel amplification technology (OCEAN2) that enables simultaneous detection and genotyping of trace amounts of mutant codon 12 Kras in a large excess of wild type DNA.

The so-called OCEAN2 (international application WO 2007/060707) technology refers to a method for simultaneous amplification and detection of nucleic acids. In particular the method for detecting a presence or an absence of a target DNA sequence in a sample, comprises the steps of:
a) contacting the sample with an oligonucleotide system under hybridization conditions so as to form a reaction mixture, said oligonucleotide system including a first oligonucleotide and a second oligonucleotide, wherein
i) at least one of said first and said second oligonucleotides includes a 5' end region comprising a recognition sequence being able to be cut by a double strand, site specific, high temperature resistant cleaving agent, said 5' end region having covalently linked at its extremities a coupled detection system so that when the recognition sequence is cleaved by said double strand, site specific, high temperature resistant cleaving agent, a signal is generated;
ii) said first oligonucleotide comprises a 3' end region able to hybridise to a complementary region of one extremity of one strand of the target DNA sequence;
iii) said second oligonucleotide comprisese a 3' end region able to hybridise to a complementary region of the opposite extremity of the other strand of the target DNA sequence;
b) adding, with appropriate substrates and cofactors, at a suitable ionic and pH environment, both a temperature resistant DNA polymerase and said double strand, site specific, high temperature resistant cleaving agent to said reaction mixture under predetermined reaction conditions, such that, if the target nucleic acid sequence is present in the sample, said first and said second oligonucleotide hybridize to the same and prime the DNA polymerase reaction to obtain a first specific amplified product;
c) cycling the hybridization of said first and said second oligonucleotide to said specific amplification product so that a second specific amplified product is extended comprising the 5' end region of the second or the first oligonucleotide, respectively, forming a double stranded recognition site for said cleaving agent so that the double strand, site specific, high temperature resistant cleaving agent cuts specifically at the recognition sequence and induces the generation of a signal by the coupled detection system;
d) detecting the generated signal.

The double strand, site specific, high temperature resistant cleaving agent is a high temperature resistant restriction endonuclease, more preferably PspGI, alternatively TliI, TfiI, BstNI, ApoI, BstBI, BstEII, SmlI, TspRI, Tsp45I or BsoBI.

The coupled detection system is a fluorophore-quencher system, preferably having the quencher at the 5' end and the fluorophore at the 3' end of the region comprising the recognition sequence; alternatively having the quencher at the 3' end and the fluorophore at the 5' end of the region comprising the recognition sequence.

Exemplified fluorophores are: Fluorescein, Tamra, Texas red, Alexa488 (Molecular Probes), Oyster-556 (Flownamics, DeNovo), Oyster-645 (Flownamics, DeNovo), Cy3 (GE-Amersham), Cy5 (GE-Amersham), Cal610 (Biosearch).

Exemplified quenchers are: BHQ1 (Biosearch), BHQ2 (Biosearch), Iowa Black FQ (IDTdna), Iowa Black RQ (IDTdna), Eclipse (Epoch/Nanogen), Qsy series (Molecular Probes).

The 5' end region of the first and second oligonucleotide further comprises spacer regions at its 5' end and/or 3' end.

The target DNA sequence is a sequence specific for an organism, preferably a pathogen organism, preferably a virus, more preferably a virus of the following species: HCV, HBV, HIV, HCMV, EBV, HPV. The temperature resistant DNA polymerase has a diminished or absent 3' exonuclease activity. Alternatively the temperature resistant DNA polymerase is able to exert its polymerising activity only at a high temperature.

The oligonucleotide system of OCEAN2 includes a first oligonucleotide and a second oligonucleotide, wherein
  i) at least one of said first and said second oligonucleotides includes a 5' end region comprising a recognition sequence being able to be cut by a double strand, site specific, high temperature resistant cleaving agent, said 5' end region having covalently linked at its extremities a coupled detection system so that when the recognition sequence is cleaved by said double strand, site specific, high temperature resistant cleaving agent, a signal is generated;
  ii) said first oligonucleotide comprises a 3' end region able to hybridise to a complementary region of one extremity of one strand of the the target DNA sequence;
  iii) said second oligonucleotide comprisese a 3' end region able to hybridise to a complementary region of the opposite extremity of the other strand of the the target DNA sequence.

The authors have now set up an assay wherein the OCEAN2 assay is modified to allow simultaneous detection of mutant alleles, and identification of the specific mutated sequence. The tested system is the identification of mutant K-ras codon 12 alleles. They are enriched and simultaneously genotyped by the presence of peptide nucleic acids (PNAs) probes in an homogeneous single tube amplification reaction.

Therefore it is an object of the invention a method for detecting the presence or the absence of a mutant DNA sequence in a sample, the method comprising the steps of:
  a) contacting the sample with an oligonucleotide system under hybridization conditions so as to form a reaction mixture, said oligonucleotide system including a reverse primer and a mutagenic primer, wherein
  i) said reverse primer includes:—a 5' end region comprising a recognition sequence being able to be cut by a high temperature resistant restriction endonuclease; said 5' end region having covalently linked at its extremities a coupled detection system so that when the recognition sequence is cleaved by said high temperature resistant restriction endonuclease, a signal is generated;—a 3' end region able to hybridise to a complementary region downstream of the putative mutant DNA sequence;
  ii) said mutagenic primer comprises:—a 5'end region comprising a recognition sequence being able to be cut by a high temperature resistant restriction endonuclease;—a 3' end region able to hybridise to a complementary region of the opposite extremity of the other strand of the sample DNA sequence, said 3' end of the mutagenic primer has a sequence so that the recognition sequence being able to be cut by the high temperature resistant restriction endonuclease is created only when said primer is extended on the wild type sequence so that the restriction endonuclease digests the amplicon and suppresses the amplification reaction; and the recognition sequence being able to be cut by high temperature resistant restriction endonuclease is not polymerised when the mutant sequence is present in the DNA sample;
  b) adding with appropriate substrates and cofactors, at a suitable ionic and pH environment, both a temperature resistant DNA polymerase and said high temperature resistant restriction endonuclease to said reaction mixture under predetermined reaction conditions, such that, if the mutant DNA sequence is present in the sample, said reverse primer and said mutagenic primer hybridize to the same and prime the DNA polymerase reaction to obtain a first specific amplified product;
  c) cycling the hybridization of said oligonucleotide system so that a second specific amplified product is extended comprising the 5' end region of the reverse primer forming a double stranded recognition site for said restriction endonuclease so that the high temperature resistant restriction endonuclease cuts specifically at the recognition sequence and induces the generation of a signal by the coupled detection system;
  d) detecting the generated signal.

Preferably the high temperature resistant restriction endonuclease is PspGI.

In a specific embodiment the mutant sequence to detect is in the human Kras gene, preferably the mutation of the human Kras gene sequence to detect is at codon 12, GGT of the human Kras wild type coding sequence.

In a preferred embodiment the coupled detection system is a fluorophore-quencher system, more preferably the fluorophore-quencher system has the fluorophore at the 3' end and the quencher at the 5' end of the recognition sequence, alternatively the fluorophore-quencher system has the fluorophore at the 5' end and the quencher at the 3' end of the recognition sequence.

In a further preferred embodiment the 5' end region of the first and second oligonucleotide further comprises spacer regions at its 5' end.

A further object of the invention is an oligonucleotide system for the simultaneous selective amplification and detection of a mutant DNA sequence in a sample, including a reverse primer and a mutagenic primer, wherein:
  i) said reverse primer includes:—a 5' end region comprising a recognition sequence being able to be cut by a high temperature resistant restriction endonuclease; said 5' end region having covalently linked at its extremities a coupled detection system so that when the recognition sequence is cleaved by said high temperature resistant restriction endonuclease, a signal is generated;—a 3' end region able to hybridise to a complementary region downstream of the putative mutant DNA sequence;
  ii) said mutagenic primer comprises: a 5' end region comprising a first recognition sequence being able to be cut by a high temperature resistant restriction endonuclease;—a 3' end region able to hybridise to a complementary region of the opposite extremity of the other strand of the sample DNA sequence, said 3' end of the mutagenic primer has a sequence so that a second recognition sequence being able to be cut by the high temperature resistant restriction endonuclease is created only when said primer is extended on the wild type sequence, so that the restriction endonuclease digests the amplicon and suppresses the amplification reaction; and the recognition sequence being able to be cut by high temperature resistant restriction endonuclease is not polymerised when the mutant sequence is present in the DNA sample.

Preferably the high temperature resistant restriction endonuclease sequence is for PspGI.

In a preferred embodiment the mutant sequence to detect is in the human Kras gene, more preferably at codon 12, GGT, of the human Kras wild type coding sequence.

In a preferred embodiment the coupled detection system is a fluorophore-quencher system, more preferably the fluorophore-quencher system has the fluorophore at the 5' end and the quencher at the 3' end of the recognition sequence, alternatively the fluorophore-quencher system has the fluorophore at the 3' end and the quencher at the 5' end of the recognition sequence. In a preferred embodiment the 5'end region of the first and second oligonucleotide further comprises spacer regions at its 5'end and/or 3' end.

It is a further object of the invention a kit for simultaneous selective amplification and detection of a mutant DNA sequence comprising the oligonucleotide system as above described and a high temperature resistant restriction endonuclease. Preferably the high temperature resistant restriction endonuclease is PspGI.

In a preferred embodiment the kit further comprises a temperature resistant DNA polymerase.

It is another object of the invention a method for identifying a specific mutated DNA sequence in a sample, comprising the steps of:

a) contacting the sample with an oligonucleotide system under hybridization conditions so as to form a reaction mixture, said oligonucleotide system including a reverse primer and a mutagenic primer as above described and further comprising a modified oligonucleotide having a sequence complementary to the specific mutated DNA sequence to be identified and being able to bind to said specific mutated DNA sequence with an higher binding affinity with respect to the unmodified oligonucleotide;

b) adding with appropriate substrates and cofactors, at a suitable ionic and pH environment, both a temperature resistant DNA polymerase and said high temperature resistant restriction endonuclease to said reaction mixture under predetermined reaction conditions, such that:

i) if the specific mutated DNA sequence is present in the sample, said modified oligonucleotide anneals to the same and does not allow the mutagenic primer to hybridize, thus blocking the amplification reaction;

ii) if the specific mutated sequence is not present in the sample, said reverse primer and said mutagenic primer hybridises to the DNA sequence allowing the reaction as above decribed.

In a preferred embodiment the modified oligonucleotoide is a peptide nucleic acid (PNA), more preferably PNA comprises a sequence complementary to mutation of the Kras gene, even more preferably to a mutation of the Kras codon 12 gene, even more preferably the PNA comprises one of the following sequences: GTT, GAT or TGT.

Another object of the invention is an oligonucleotide system comprising the reverse primer, the mutagenic primer and further the modified oligonucleotide as above described.

Another object of the invention is a kit for the identification of a specific mutated DNA sequence comprising the oligonucleotide system as described above.

Figure 2:
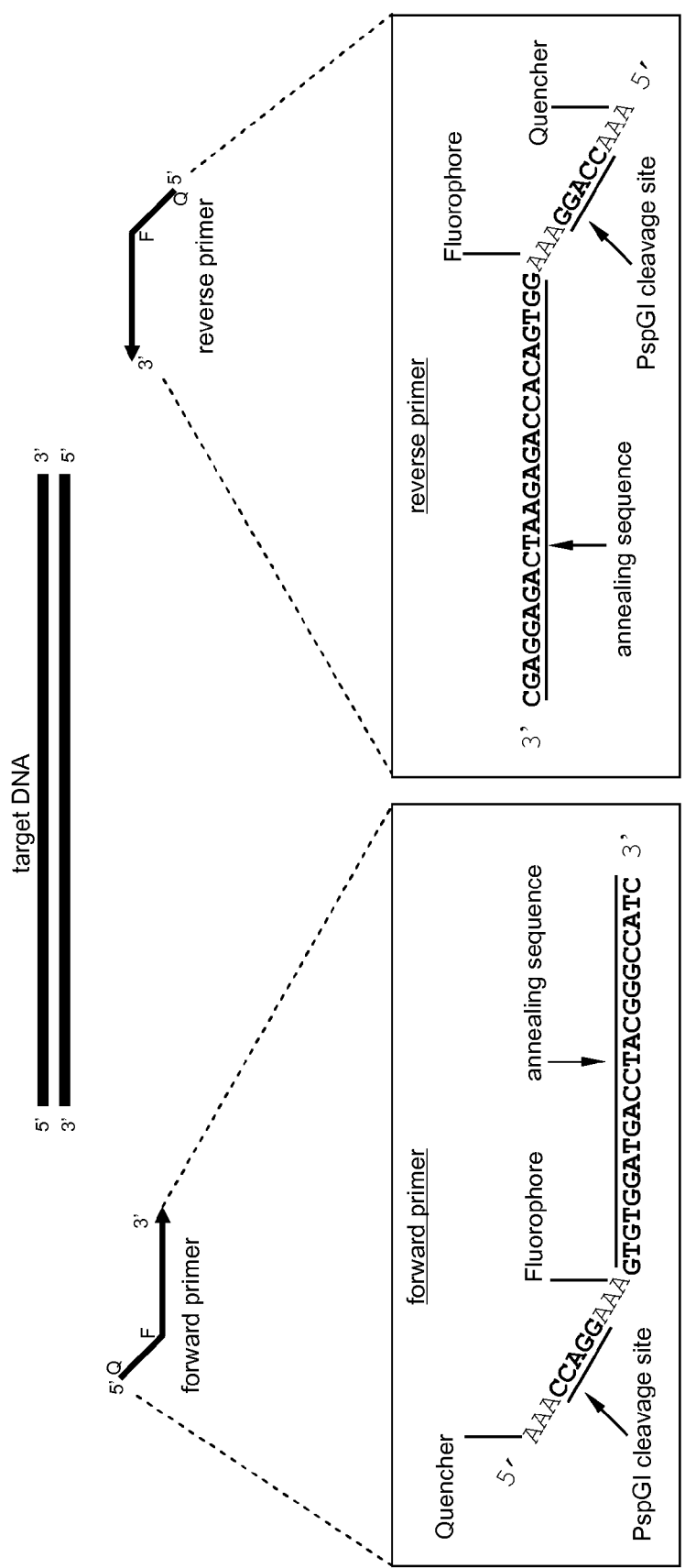
Figure 3:
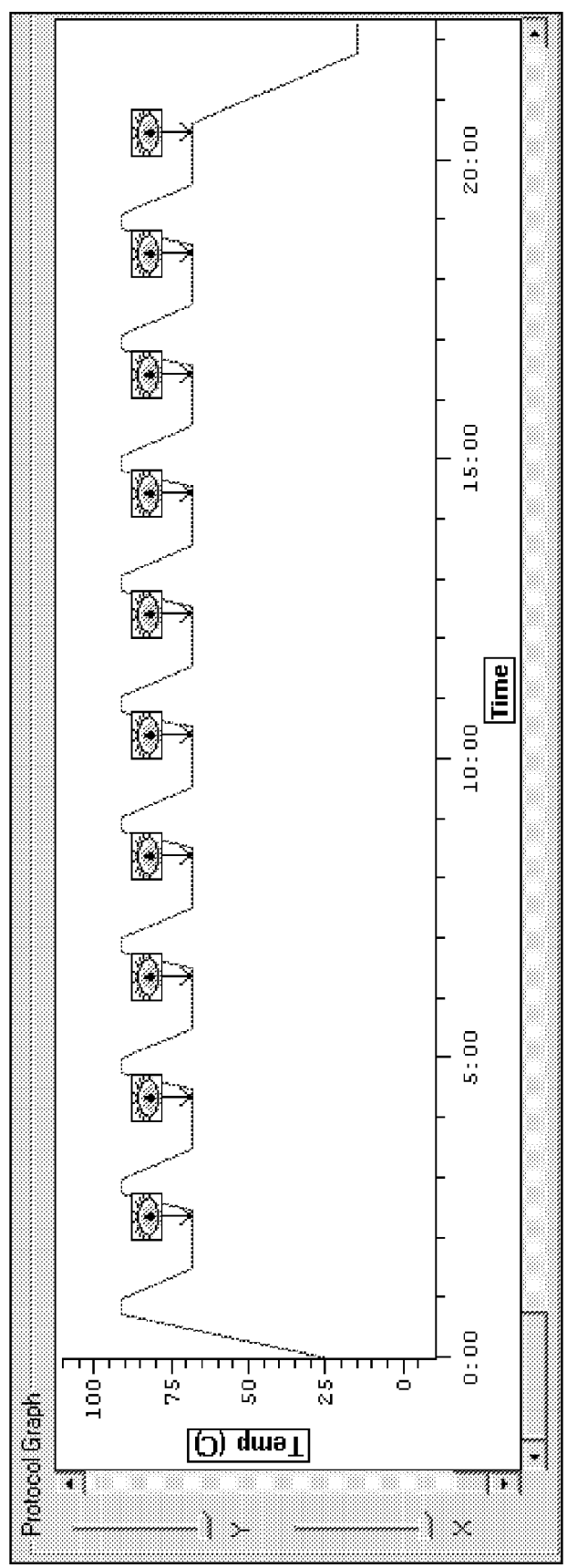

The invention will be described with reference to specific not limiting examples, including the following figures:

FIG. 1. Schematic diagram of the OCEAN2 method;

FIG. 2. Schematic diagram of the oligonucleotides for OCEAN2;

FIG. 3. Example of programmed cycles, the eye indicates the fluorescence detection step.

FIG. 4. Panel A: Quantification of HCMV DNA sequences using the OCEAN2 assay. Amplification plots of 10-fold serial dilutions of HCMV genomic DNA containing $2 \times 10^6$-$2 \times 10^1$ starting copy number and a no-template control. Panel B: Calibration curves generated using the MJ Opticon3 software where Ct (threshold cycle derived from 4A) is plotted against starting quantity (copy number; $R^2$=0.999). Panel C: Agarose gel electrophoresis of reaction product. Fluorescence was detected on a Typhoon 9200 (Amersham) for Ethidium Bromide (EtBr) at 532/610 nm and for AlexaFluor 488 fluorophore (488) at 532/526 nm.

Figure 5A:
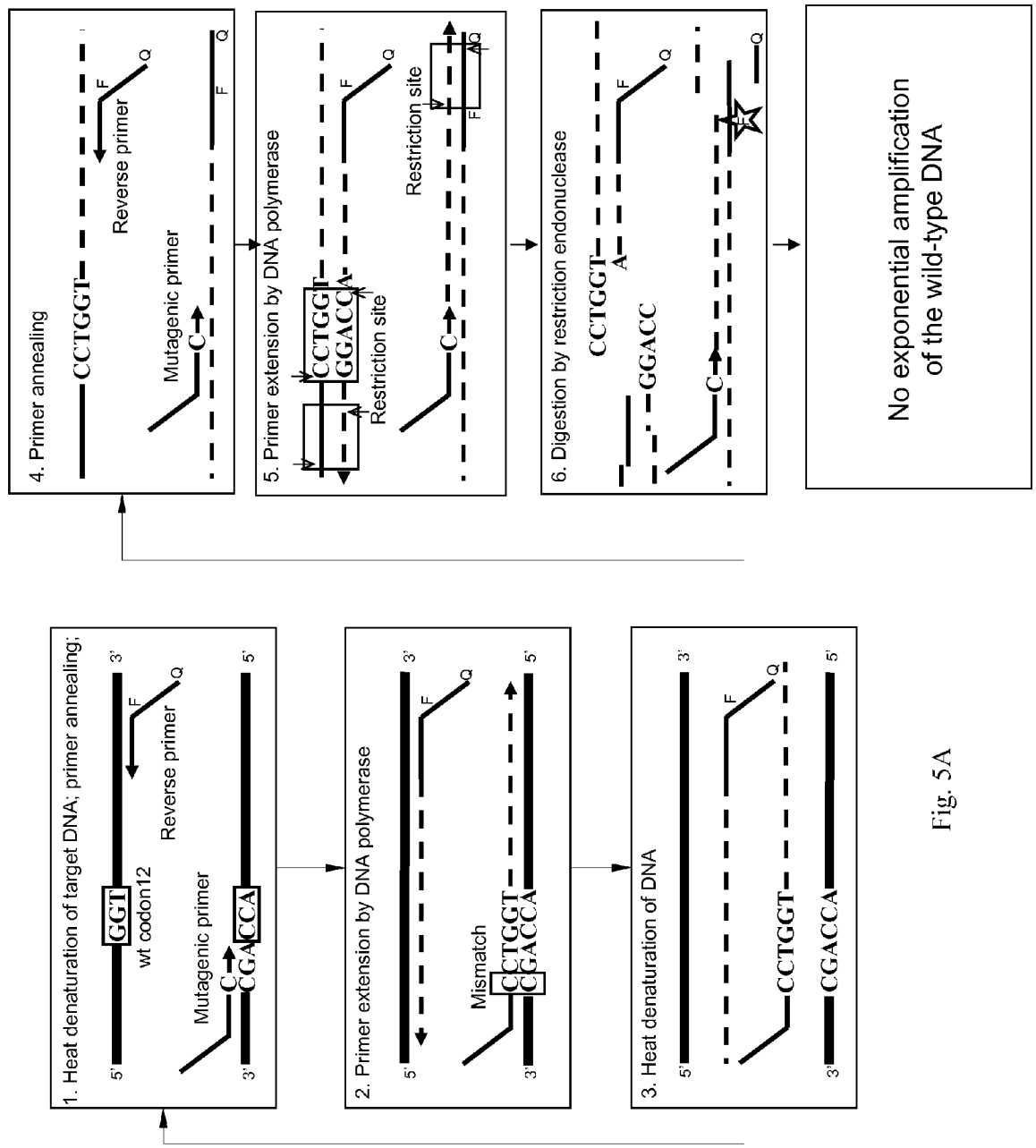
Figure 5B:
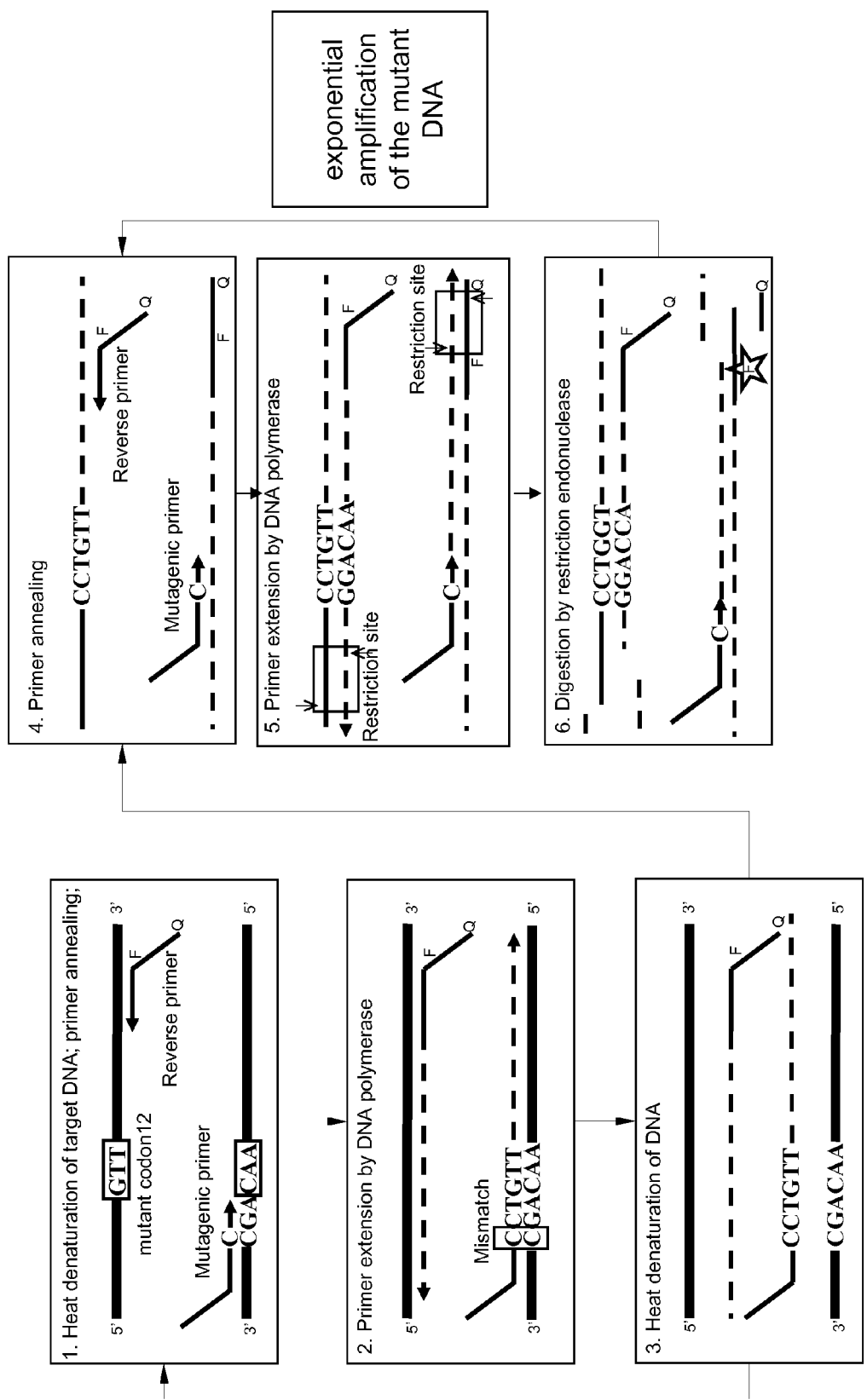

FIG. 5. A and B Selective Ocean2 principle. The Selective OCEAN2 assay consists in an amplification of the gene region of interest using a specific primer pair designed to carry a 11-base sequence tag at 5'-end, containing the recognition site for a thermostable endonuclease. The reverse primer is double-labelled on the tag region with a quencher and a fluorophore. During the extension by polymerase chain reaction, the primer tag region becomes double stranded, available for the recognition and digestion by the endonuclease. Double labeling of the reverse primer generates a fluorescent signal by eliminating fluorescent quenching each time the tag is digested by the endonuclease in solution. To enrich the mutant alleles (FIG. 5B) the forward primer is mutagenic: the variation introduced creates the recognition site for the thermostable enzyme already present in solution only when the codon 12 sequence is GGT (wild type). In these cases, represented in the left side of the picture, the endonuclease digests the amplicon suppressing the amplification reaction. Differently, as shown in the right part of the picture, the mutant alleles carried a nucleotide variation in the codon 12, result in an absence of PspGI recognition site. The amplicon can be consequently produced. In this way, adding the same endonuclease at the reaction solution, a double function of mutant enrichment and signal generation monitorable in Real Time is obtained.

Figure 6:
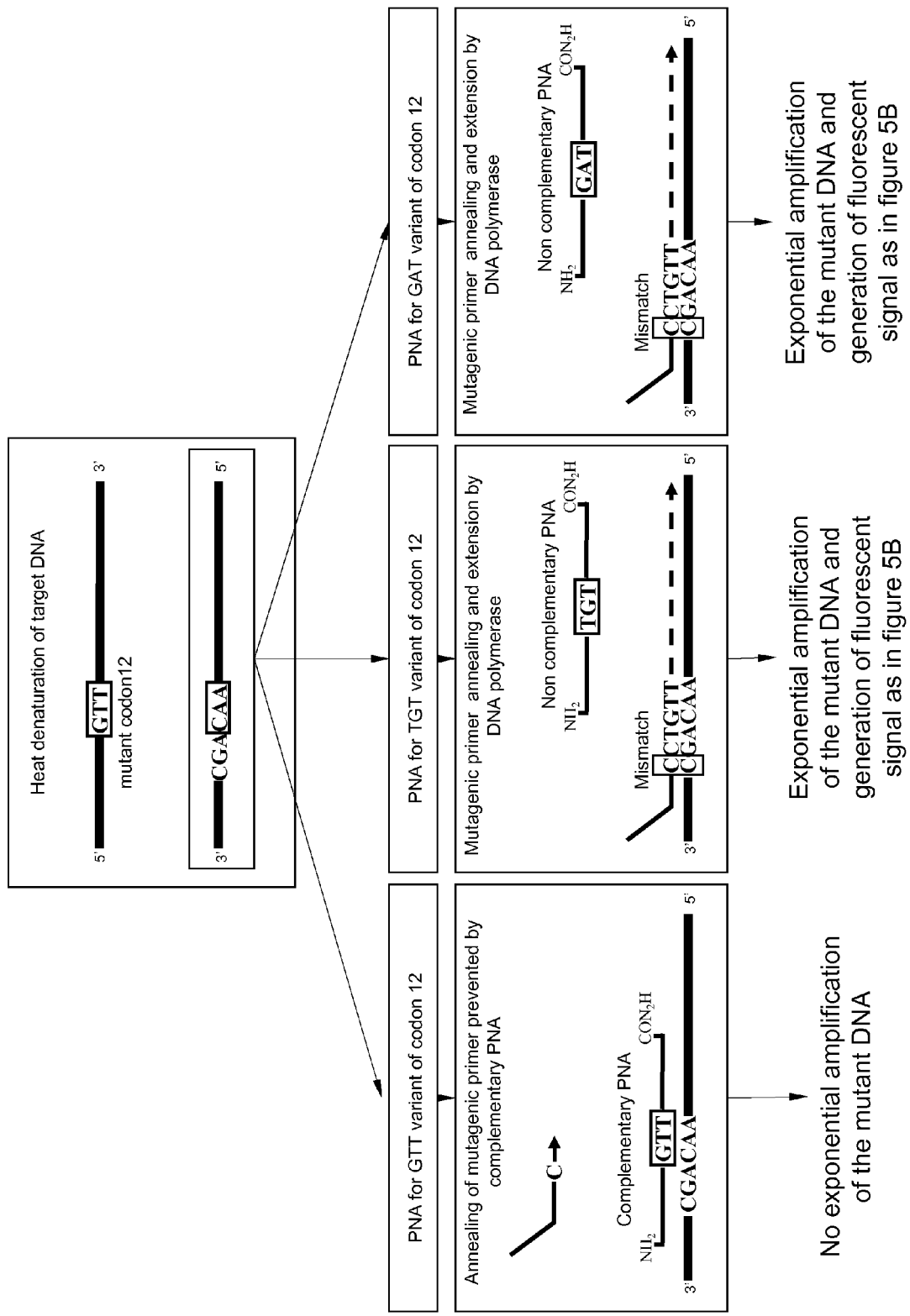

FIG. 6. Selective PNA-mediated OCEAN2. To obtain an homogeneous mutant enrichment and genotyping, the Selective OCEAN2 reaction is carried out in parallel reactions, each one in presence of a different PNA probe, specific for the most common codon 12 variation: GTT, GAT, TGT. During the REMS PNA mediated OCEAN2 no amplification products are obtained either from the wild type alleles (left side of the figure) which are digested by the endonuclease in solution, or from the mutant alleles which are binded by the PNA specific present in solution. As shown in the right panel, GTT mutant allele produces fluorescent signals from the reactions containing PNA not complementary to its codon 12 sequence. Observing the amplification products of each reaction performed, a signal is visible for each assay except for the one performed in presence of the PNA complementary to the mutation of the target DNA analyzed.

Figure 7:
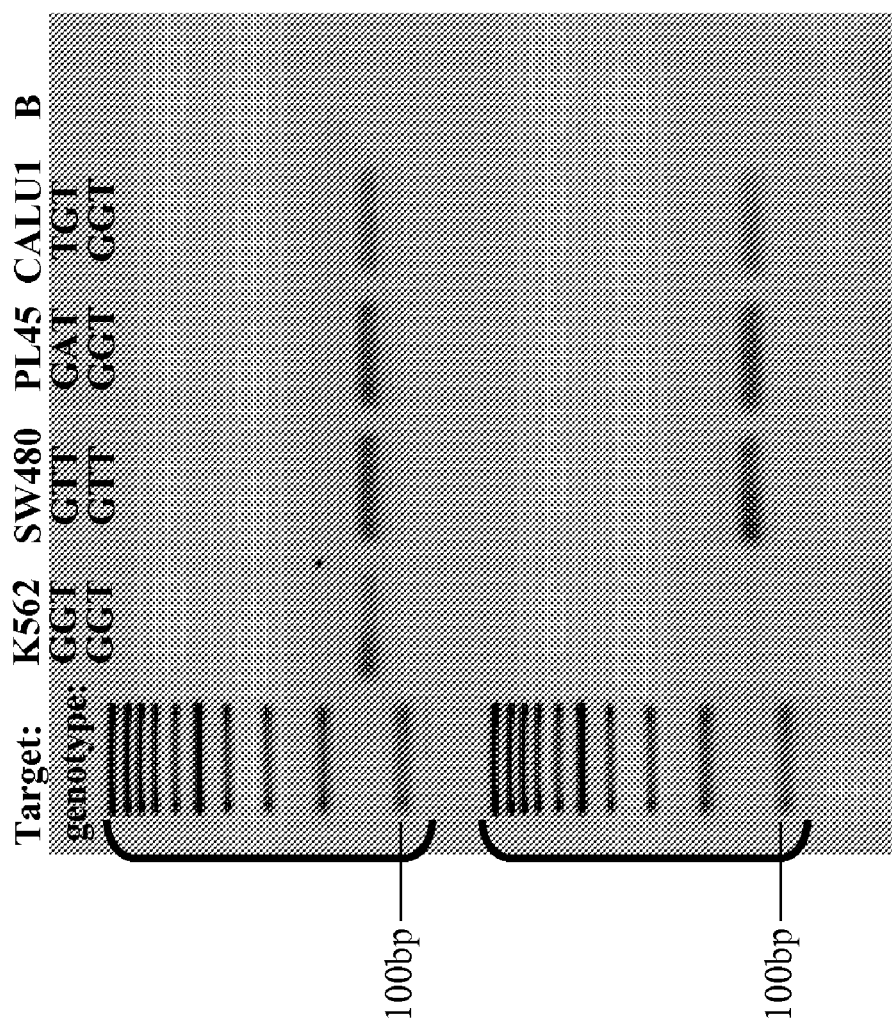

FIG. 7. Validation of the Selective -OCEAN2 principle on cell lines. OCEAN2 reaction performed on wild type GGT cell line (K562) and mutant cell lines SW480 (GTT/GTT), PL45 (GGT/GAT) and CALU1 (GGT/TGT) in presence of a mutagenic forward primer, which creates the recognition site for the thermostable enzyme in the codon 12 GGT alleles. To demonstrate the principle, the reaction was performed in parallel in absence (upper gel) and presence (lower gel) of the endonuclease and separated on ethidium-stained agarose gel. As shown, when the enzyme is added, the wild type target DNA amplification is suppressed.

Figure 8:
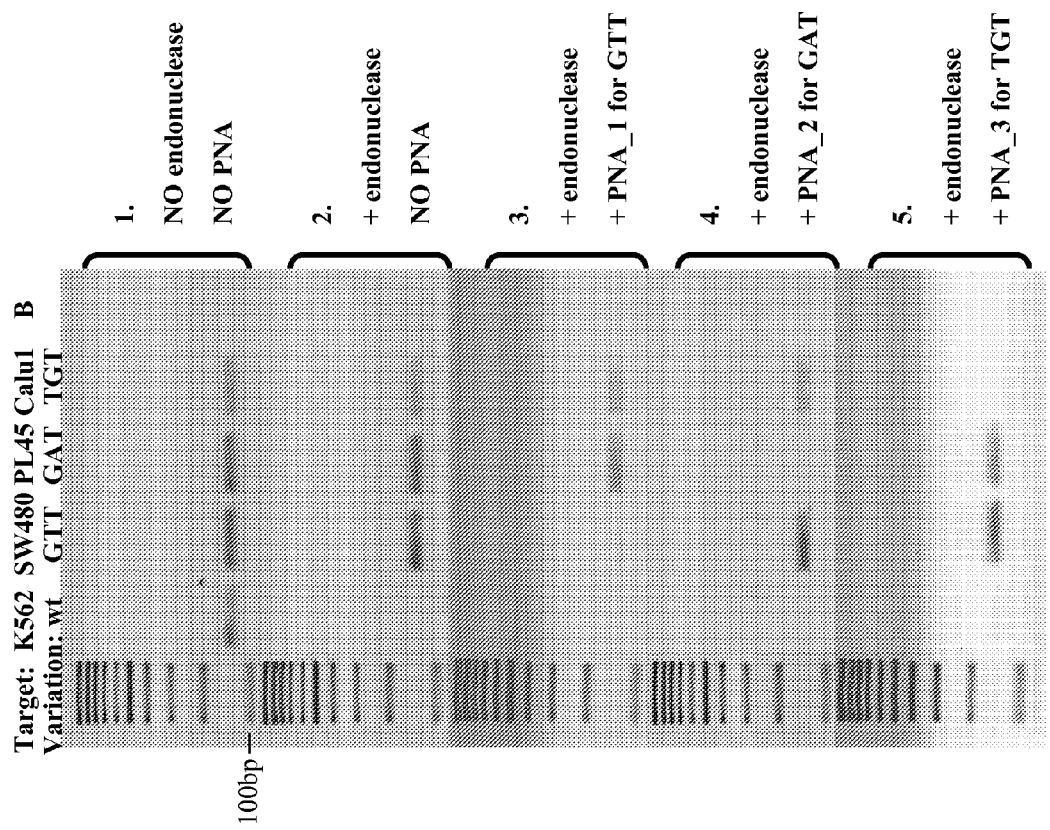

FIG. 8. Validation of the Selective PNA-mediated OCEAN2 principle on cell lines. To enrich and simultaneously genotype the codon 12 variation sequences present in the control cell lines, three additional reactions with a different PNA probe specific for the mutations in analysis were performed and the results compared with the one obtained from a parallel reaction in absence of PNA.

The first row shows the reaction products obtained after a Selective OCEAN2 assay in absence of the enzyme PspGI (control of the functionality of the OCEAN2 amplification). The bands visible on the second row come from a Selective OCEAN2 reaction in presence of the endonuclease, and represents the amplification products from mutant alleles (detection of mutant versus wild type samples). The amplification products shown in the third line were obtained by a Selective OCEAN2 in presence of PspGI and PNA__1 specific for the GTT codon 12 sequence. The band disappeared in respect to the second row is the one coming from the reaction on the cell line SW480 (GTT/GTT), for which the PNA is specific. The reaction shown in the forth line is performed in presence of the enzyme PspGI and the PNA__2 specific for the suppression of GAT alleles. No bands from the cell line PL45 (GGT/GAT) are obtained, due to the endonuclease digestion and PNA suppression. In the last fifth line results from the assay performed adding PspGI and PNA__3 (specific for TGT codon 12) are shown. Cell lines characterized by a codon 12 variation different than TGT gave a clear band on gel, while the CALU 1 sample (TGT/GGT) was not amplified. The correct genotype is assigned to each cell lines analysed by comparison between the amplification products of the five parallel homogeneous reactions performed.

Figure 9:
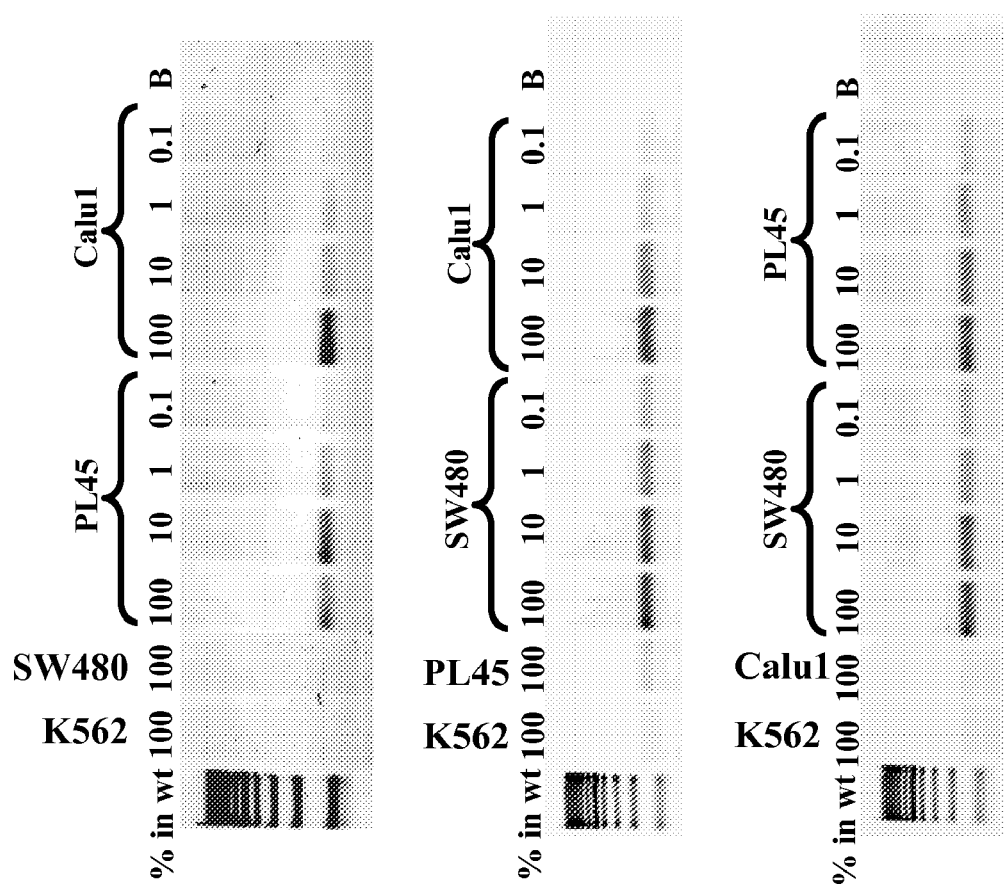

FIG. 9. Sensitivity of Selective PNA-mediated OCEAN2 assay. To examine the sensitivity of the PNA mediated Selective OCEAN2 assay, genomic DNA from the mutant cell lines SW480, PL45 and CALU1 were diluted into wild-type K-ras codon 12 DNA from K562 cells to obtain decreasing ratios of mutant-to-wild type alleles, 100%, 10%, 1%, 0.1%, 0%. For each target mixture a Selective OCEAN2 assay was performed in presence of a different PNA specific for all the codon 12 variations represented. Each row of the image shows the results of the assay obtained in presence of a different PNA (PNA able to suppress alleles GTT, GAT, TGT respectively). The second lane of each row comes from a reaction performed on 100% cell line carrying the genotype complementary to the PNA present in solution. The other six lanes show the products obtained from the assay performed on the wild type/mutant mixtures from cell lines with a sequence in codon 12 not specific for the PNA in solution. An amplification product is still present in samples composed by 0.1% mutant allele and 99.9% wild type allele.

Figure 10:
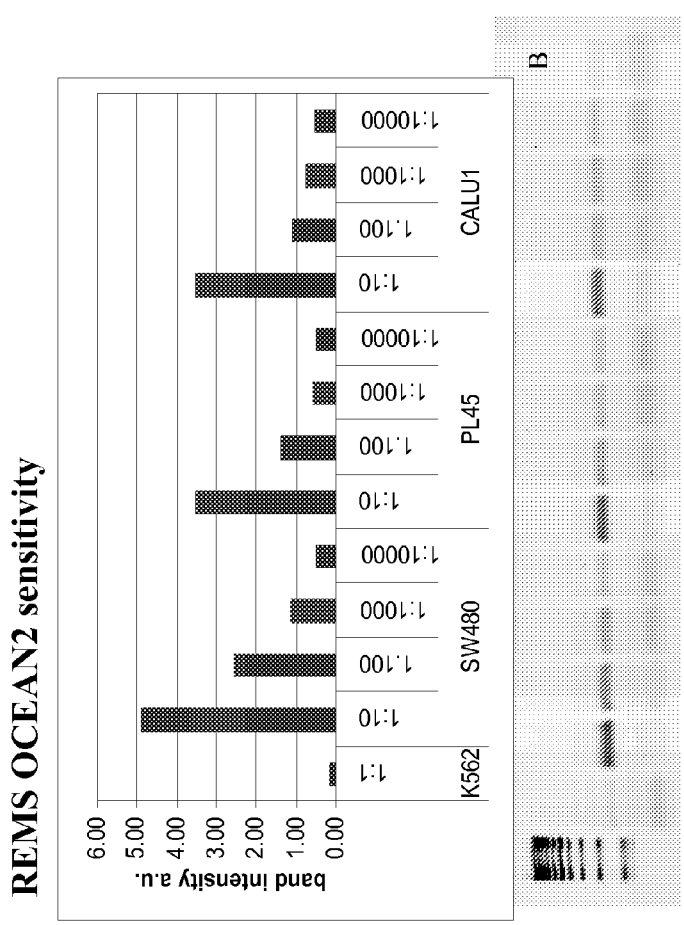

FIG. 10. The REMS OCEAN2 assay was performed on cell lines K562 (homozygous wild type), and on mutant cell lines SW480 (GTT/GTT), PL45 (GGT/GAT) and CALU 1 (GGT/TGT) serially diluted into wild type DNA to obtain mixtures in which mutant to wild type ratio is 1:10, 1:100, 1:1000 and 1:10000. After 38 cycles, the reaction solutions were separated on agarose gel and the bands obtained were quantified by ImageQuant™ Software (Amersham Biosciences) after blank subtraction. As shown in the figure, Selective OCEAN2 assay can detect the mutant allele even when it is present in 0.01% of the sample analyzed.

MATERIAL, METHODS AND RESULTS OF THE OCEAN2 ASSAY

Reagents
HCMV DNA control (Tebu-bio, 08-701-000), referred to as "target"
Primers: ES69QF and ES70QF, synthetized by IDT-DNA technologies, Coralville, Iowa, "primers" (sequences attached)
Reaction buffer: 10× stock is composed as follows: 100 mM TrisHCl, 500 mM NaCl, 500 mM KCl, pH 8.0; all reagents from Sigma, "buffer"
MgCl2 100 mM (Sigma), "MgCl2"
dNTPs mix 10 mM (Fermentas), "dNTPS"
Formamide 100% (Sigma), "Formamide"
BSA 100× (New England Biolabs), "BSA"
Taq DNA Polymerase recombinant 5 U/ul (Fermentas), "Taq"
PspGI 10 U/ul (New England Biolabs), "PspGI"
Sterile apyrogen water (SALF Spa), "ddw"
Materials
PCR sample cooler (Eppendorf) for sample preparation, "on ice"
Tubes, pipettes and tips (Eppendorff, Finnpipette, ART) for sample preparation, "plasticware"
Gloves
0.2 ml low-profile strip tubes and caps for reaction, "strips"
Nanodrop ND-1000 spectrophotometer (Nanodrop technologies, Wilmington, Del.), "Nanodrop"
Thermal cycler equiped with fluorescence detector, Chromo-4 (MJ research, BioRad), "thermal cycler"
Procedure
1. Sample Preparation
Dilute primers (shipped as powder) to a 100 µM stock solution with ddw. Check for correct concentration using absorbance at 260 nm, according to manufacturer's instructions. Prepare a 10 µM working dilution in ddw. Stock in aliquots. It is better to store stock solutions at −20° C., while working dilutions should be stored at 4° C.
Prepare buffer and MgCl$_2$ in ddw. Prepare a 1× dilution of BSA in ddw.
Prepare reaction mix as follows: 0.375 µM primers, 1× buffer, 2 mM MgCl$_2$, 5% Formamide, 0.3 mM dNTPs, 0.025 U/µl Taq, 0.5 U/µl PspGI. Final volume of the reaction mix must be ¾ of the total reaction volume (i.e. 15 µl reaction mix+5 µl sample). Always keep reagents on ice. Prepare mix at least for 6 standard samples and 1 negative sample, plus the number of unknown samples to test. An example of volumes to mix for 6 standards and 1 negative samples is shown in Table 1 (all volumes in microliters).

TABLE 1

Sample mix composition

| | Sample tube | | | | | | |
|---|---|---|---|---|---|---|---|
| | 1 | 2 | 3 | 4 | 5 | 6 | 7 |
| target dilution to add (5 µl): cps/µl | 4 | $4*10^1$ | $4*10^2$ | $4*10^3$ | $4*10^4$ | $4*10^5$ | |
| ES69QF 10 µM | 0.75 | 0.75 | 0.75 | 0.75 | 0.75 | 0.75 | 0.75 |
| ES70QF 10 µM | 0.75 | 0.75 | 0.75 | 0.75 | 0.75 | 0.75 | 0.75 |
| HB pH 8.0 10x | 2 | 2 | 2 | 2 | 2 | 2 | 2 |
| MgCl$_2$ 100 mM | 0.4 | 0.4 | 0.4 | 0.4 | 0.4 | 0.4 | 0.4 |
| Formamide 100% | 1 | 1 | 1 | 1 | 1 | 1 | 1 |
| dNTPs 10 mM | 0.6 | 0.6 | 0.6 | 0.6 | 0.6 | 0.6 | 0.6 |
| Taq Polymerase 5 U/µl | 0.1 | 0.1 | 0.1 | 0.1 | 0.1 | 0.1 | 0.1 |
| PspGI 10 U/µl | 1 | 1 | 1 | 1 | 1 | 1 | 1 |
| ddw to 15 µl | 8.4 | 8.4 | 8.4 | 8.4 | 8.4 | 8.4 | 13.4 |

Vortex reaction mix for 5 seconds and quickly spin down for 15 seconds at low speed. Always keep the reaction mix on ice from now on.

Dispense 15 µl of reaction mix in the strip. Keep the strips on ice.

Start adding 5 µl of samples to the strips. Always follow this order: BSA 1× in the negative sample tube, (close the tube), unknown samples. Close all these tubes before continuing. Keep the strips on ice. Change gloves.

Prepare serial dilutions of the target ("target dilutions") from shipped solution. Shipped solution is a $1.8*10^8$ copies/µl Dilute initially to a $4*10^5$ copies/µl in 1× BSA, then dilute serially (1:10) in 1× BSA to $4*10^4$ copies/µl, $4*10^3$ copies/µl, $4*10^2$ copies/µl, $4*10^1$ copies/µl, 4 copies/µl. Put the target dilutions on ice. Change gloves.

Add 5 µl of target dilutions to the strips. Add 5 µl of the target dilutions starting from the less concentrated one to the most concentrated one. Close all the tubes. Keep the strips on ice. Discard gloves.

2. Reaction

The reaction follows the method scheme of FIGS. 1 and 2.

Program the amplification cycles in order to obtain the following protocol: 50 cycles of denaturation at 90° C. for 15 seconds, annealing-extension-digestion at 68° C. for 1 minute. Include at the end of annealing-extension-digestion step, the fluorescence detection for the appropriate fluorophore (see primers sequence below). An example of programmed cycles is described in FIG. 3.

Start the protocol. If the thermal cycler requires some minutes to heat the lid to the proper working temperature, keep the strips on ice until the heating has finished. Put the strips in the thermal cycler immediately before the beginning of the cycles.

3. Data Analysis

Enable baseline subtraction. Since in the first 3-5 cycles there is a slight increase of fluorescence, do not set baseline as the first fluorescence measured, but as the average fluorescence measured in the first 5-15 cycles (as long as no exponential curve rises up in the considered cycles)

Enable blank subtraction.

Set threshold as "2 * standard deviation over the considered cycle range". Alternatively, try to fit the threshold so that $R^2$ value (coefficient of linear regression) is as close as possible to 1. In this case, discard a threshold that is below the value that equals "1*standard deviation over cycle range".

4. Sequences of Primers ES69QF and ES70QF

```
ES69QF
                                       (SEQ ID No. 1)
(modifications: Iowa black FQ on base 1, Alexa
Fluor 488 NHS ester on base 11)
Iowa Black
FQ ▼           ▼Alexa 488n
5' AAACCAGGAAAGTGTGGATGACCTACGGGCCATC 3'

ES70QF
                                       (SEQ ID No. 2)
(modifications: Iowa black FQ on base 1, Alexa
Fluor 488 NHS ester on base 11)
Iowa Black
FQ ▼           ▼Alexa 488n
5' AAACCAGGAAAGGTGACACCAGAGAATCAGAGGAGC 3'
```

5. Results

The linear range of quantification of the assay for HCMV target DNA was assessed. Samples were prepared according to Table 1. Results are shown in FIG. 4. To determine the linear range and to develop a calibration curve for purposes of quantification, ten-fold serial dilutions of HCMV genomic DNA consisting of $2\times10^6$-$2\times10^1$ target copy number were analysed (FIG. 4A). FIG. 4B shows that the dynamic linear range was at least 5 orders of magnitude, from $2\times10^6$ to $2\times10^1$ target copy number. The correlation coefficient of the calibration curve was greater than 0.99.

Specificity of the assay for HCMV target was demonstrated by the consistent lack of amplification in the no-template control even after 50 cycles.

End point analysis on an agarose gel stained with EtBr shows that a single specific amplification product is obtained starting from any dilution tested. The same gel scanned on a Typhoon 9200 laser scanner (Amersham) at 532/526 nm shows that the PCR products contain the fluorescent dye (Alexa Fluor 488). In the bottom part of the gel the unreacted primers reflect the efficiency of the amplification reactions, being progressively more consumed with increasing starting target copy number. No primer-dimer is observed, even after 50 cycles.

Materials and Methods of Selective PNA-Mediated OCEAN2 Assay

The Selective PNA-mediated OCEAN2 assay is an homogeneous single tube amplification reaction in which the mutant Kras codon 12 alleles are enriched and simultaneously genotyped by the presence of PNAs probes.

As described above, the OCEAN2 assay consists in an amplification of the gene region of interest using a specific primer pair designed to carry a 11-base sequence tag at 5'-end, containing the recognition site for an endonuclease. The reverse primer is double-labelled on the tag region with a quencher (in 5') and a fluorophore (in 3') as shown in table 2. During the extension by polymerase chain reaction, the primer tag region becomes double stranded, available for the recognition and digestion of the endonuclease PspGI, which is a thermostable enzyme alive during the thermal cycles of the amplification reaction. Double labeling of the reverse primer generates a fluorescent signal by eliminating fluorescent quenching each time the tag is digested by the endonuclease in solution.

The enrichment of mutant components is permitted by the presence of a mutagenic forward primer complementary to the kras gene region containing the codon 11 and 12 (FIG. 5). The variation introduced creates the recognition site for the thermostable enzyme PspGI only when the codon 12 sequence is GGT (wild type). In these cases the endonuclease already present in the reaction mix digests the amplicon suppressing the amplification reaction. Differently, the mutant alleles carrying a nucleotide variation in the codon 12, results in an absence of PspGI recognition site. The amplicon can be consequently produced. In this way, a double function of mutant enrichment and signal generation monitorable in Real Time is obtained adding the same endonuclease at the reaction solution, To genotype the amplification products obtained (FIG. 6), for each sample different Selective reaction are conducted, each one adding a different Peptide Nucleic Acid probe specific for all the most common Kras codon 12 mutations. PNAs are non extendable oligonucleotides where the ribose-phosphate backbone is replaced by (2-aminoethyl)-glycine units linked by amide bonds. This synthetic oligomers form duplex DNA/DNA with higher thermal stability then DNA/DNA, but which are significantly destabilized in the case of a single mismatched (17). Observing the amplification products of each reaction performed, a signal is visible for each assay except for the one performed in presence of the PNA complementary to the mutation of the target DNA analyzed.

Source and Extraction of Genomic DNA

To verify the specificity and selectivity of PNA-PCR/OCEAN, genomic DNA from cultured cell lines SW480 (homozygous GTT), PL45 (heterozygous GAT/GGT) and CALU 1 (heterozygous TGT/GGT), obtained from the American Type Culture Collection, (Manassas, Calif., USA) was extracted by the NucleoSpin™ Tissue kit (Macherey-Nagel, Duren, Germany).

Enrichment and Genotyping of Mutants Using Selective PNA-Mediated OCEAN2 on Cell Lines with K-Ras Mutations A Selective OCEAN2 protocol, using as restriction endonuclease the thermostable PspGI enzyme, was used to digest wild type K-ras alleles during the OCEAN2 reaction, in combination with the selective suppression by Peptide Nucleic Acids (PNA) for the genotype determination of the variation enriched. PNA forms a stable duplex only with the complementary sequence of K-ras codon 12, preventing the annealing and extension of the forward primer during OCEAN2 and therefore suppress the correspondent mutant allele amplification. The authors designed and synthesized (Eurogentec, Liege, Belgium) 3 PNA probes (Table 2) specific for the Kras codon 12 mutations GTT, GAT and TGT.

The primers used in the assay were 300 nM GA111 (forward) and 300 nM GA112 (reverse) (see Table 2). The forward primer is mutagenic to create the recognition site for PspGI only in the wild type templates.

In each reaction, 68 ng of genomic DNA wild type from cell line K562 and mutant from SW480 (homozygous GTT/GTT), PL45 (heterozygous GAT/GGT) and Calu1 (heterozygous TGT/GGT) was used as a template. The reaction was performed for 35 cycles as follows: denaturation step at 94° C. for 10 sec, primers annealing at 56° C. for 30 sec, PNA annealing and primers extension at 72° C. for 60 sec. The reaction mix contained 0.1× BD Titanium™ Taq polymerase, 1× PCR buffer (BD Biosciences), 200 μM dNTPs, 1.5 mM MgCl₂ in 20 μl total volume (reaction mixA). The reaction mixA was splitted in five reactions, performed in parallel and compared each other:

First reaction: OCEAN2 without restriction endonuclease or PNA, to verify the success of the assay (positive controls).

Second reaction: OCEAN2 with addition of 0.5 U/μl PspGI (New England Biolabs). The bands that disappear in respect to the first reaction represent the wild type samples, digested by the restriction endonuclease that recognized its site (5'-CCTGG-3').

Third reaction: OCEAN2 with addition of 0.5 U/μl PspGI and 300 nM PNA_1 (table 2) specific for codon 12 GTT mutation template. The wild type bands disappear in respect to the first reaction thanks to the PsPGI digestion as well as the bands coming from the mutant cell line SW480 (homozygous GTT/GTT) which are binded and suppressed by the PNA.

Forth reaction: OCEAN2 with addition of 0.5 U/μl PspGI (New England Biolabs) and 200 nM PNA_2 (table 2) specific for codon 12 GAT mutation template. No bands from cell line PL45 (mutant GAT/GGT) are obtained thanks to the specific PNA suppression and PspGI digestion.

Fifth reaction: OCEAN2 in presence of 0.5 U/μl PspGI (New England Biolabs) and 200 nM PNA_3 (Table 2). No amplification products are obtained from OCEAN2 reactions carried out on wild type samples or mutant TGT targets (heterozygous cell line CALU1).

The products of each reaction described were examined via ethidium-stained gel electrophoresis.

By the comparison between the five parallel reactions, the mutants samples are detected and genotyped in an homogeneous way.

TABLE 2

Primers and PNA probes. The italic sequences represent the primers tag. The underlined base in GA111 sequence is the mutagenic one.

| OLIGO NAME | SEQUENCE |
|---|---|
| GA111, Fw mutagenic primer | 5' *TTTCCTGGTTTGAATATAAACTTGTGGTAGTTGGA<u>C</u>CT* 3' (SEQ ID No. 3) |
| GA112, Rv primer | 5' *TTTCCTGGTTTAGATTTACCTCTATTGTTGGATCATAT* 3' (SEQ ID No. 4) |
| GA112QF, Rv labelled primer | /5IAbFQ/*TTTCCTGGTTT*/iFluorT/ AGATTTACCTCTATTGTTGGATCATAT (SEQ ID No. 5) |
| PNA_1 specific for GTT | NH₂-GGACCTGTTGGCGTA-CON₂H (SEQ ID No. 6) |
| PNA_2 specific for GAT | NH₂-GGACCTGATGGCGTA-CON₂H (SEQ ID No. 7) |
| PNA_3 specific for TGT | NH₂-GGACCTTGTGGCGTA-CON₂H (SEQ ID No. 8) |

Results of Selective PNA-Mediated OCEAN2 Assay
Validation of the Selective OCEAN2 Principle on Cell Lines To obtain a suppression of the wild type alleles in the samples analysed, the OCEAN2 reaction was performed in presence of a mutagenic forward primer, which creates the recognition site for the thermostable enzyme PspGI in the codon 12 GGT alleles. To demonstrate the principle, the performed the reaction in parallel in absence and presence of the endonuclease on the cell lines K562, SW480, PL45 and CALU1. As showed in FIG. 7, when the enzyme is added, the wild type target DNA is suppressed (no band visible on ethidium-stained gel).

Validation of the PNA Mediated Selective OCEAN2 Principle on Cell Lines

To enrich and simultaneously genotype the codon 12 variation sequences present in the control cell lines, three additional reactions with a different PNA probe specific for the mutations in analysis were performed and the results compared with the one obtained from parallele reaction in absence of PNA (FIG. 8). The first row of the image shows the reaction products obtained after a Selective OCEAN2 assay in absence of the enzyme PspGI (control of the functionality of the amplification). The bands visible on the second row come from a Selective OCEAN2 reaction in presence of the endonuclease, and represent the amplification products from mutant alleles (detection of mutant versus wild type samples). The amplification products shown in the third line were obtained by a Selective OCEAN2 in presence of PspGI and PNA_1 specific for the GTT codon 12 sequence. The band disappeared in respect to the second row is the one coming from the reaction on the cell line SW480 (GTT/GTT), for which the PNA is specific. The reaction shown in the forth line is performed in presence of the enzyme PspGI and the PNA_2 specific for the suppression of GAT alleles. No band from the cell line PL45 (GGT/GAT) are obtained, thanks to the impossible amplification of both the alleles respectively by endonuclease digestion and PNA suppression. In the last fifth line results from the assay performed adding PspGI and PNA_3 (specific for TGT codon 12) are shown. Cell lines characterized by a codon 12 variation different than TGT gave a clear band on gel, while the CALU 1 sample (TGT/GGT) was not amplified. Observing and comparing the amplification products of the five parallel homogeneous reactions, is possible to assign the right genotype to each cell lines analyzed.

Selectivity of Selective OCEAN2 on Cell Lines

To determine selectivity of the method, restriction endonuclease-mediated selective polymerase chain reaction (REMS) OCEAN2 assay was performed on cell lines K562 (homozygous wild type), and on mutant cell lines SW480 (GTT/GTT), PL45 (GGT/GAT) and CALU 1 (GGT/TGT) serially diluted into wild type DNA to obtain mixtures in which mutant to wild type ratio is 1:10, 1:100, 1:1000 and 1:10000. After 38 cycles, the reaction solutions were separated on agarose gel and the bands obtained were quantified by ImageQuant™ Software (Amersham Biosciences) after blank subtraction. As shown in FIG. 10, REMS-OCEAN2 assay can detect the mutant allele even when it is present in 0.01% of the sample analyzed. This degree of selectivity is allowed by the extreeme thermal stability of the restriction endonuclease PspGI. Current protocols based on other thermophilic (19) enzymes require multi-step approaches to reach similar results. Based on these results we can approach homogenous detection and genotyping of mutations present at very low percentages. This could have particularly interesting implications for the detection and genotyping of these mutations in plasma.

Sensitivity of Selective PNA Mediated OCEAN2

To examine the sensitivity of the Selective PNA mediated OCEAN2 assay, genomic DNA from the mutant cell lines SW480, PL45 and CALU1 were diluted into wild-type K-ras codon 12 DNA from K562 cells to obtain decreasing ratios of mutant-to-wild type alleles, 100%, 10%, 1%, 0.1%, 0%. For each target mixture a Selective OCEAN2 assay was performed in presence of a different PNA specific for all the codon 12 variations represented. The reaction mixtures contained 68 ng total genomic DNA, 300 nM mutagenic forward primer GA111 (table 2), 300 nM reverse primer GA112 (Table 2), 0.1× BD Titanium™ Taq polymerase, 1× PCR buffer (BD Biosciences), 0.5 U/μl endonuclease PspGI (New England Lab), 200 μM dNTPs, 1.5 mM $MgCl_2$ and PNA in concentration of 500 nM if specific for codon 12 GTT (PNA_1, Table 1), 350 nM if specific for GAT (PNA_2, Table 2), 400 nM if specific for variation TGT (PNA_3, Table 2). After a denaturation step at 94° C. for 10 sec, a primer annealing step at 56° C. for 30 sec was performed, followed by a final step of PNA annealing and primers extension at 72° C. for 60 sec. After 38 cycles, the amplification products were separated by electrophoresis on 2% agarose gel and stained with ethidium bromide. Results are shown in FIG. 9. Each row of the image contains the results of the assay in presence of a different PNA (PNA able to suppress alleles GTT, GAT, TGT respectively). The second lane of each row come from a reaction performed on 100% cell line carrying the genotype complementary to the PNA present in solution. The other six lanes show the bands obtained from the assay performed on the wild type/mutant mixtures from cell lines with a sequence in codon 12 not specific for the PNA in solution. An amplification product is still present in samples composed by 0.1% mutant allele and 99.9% wild type allele. It means that the PNA approach is enough specific to avoid the suppression of alleles which sequence presents a mismatch with the PNA used, and that the assay is able to detect the presence of the mutant allele down to wariant-to wild tune 0.1% ratio.

REFERENCES

1. Srivastava S, Verma M, Henson D E. Clin Chem 2001; 7, 1118-1126.
2. Hirsch F R, Franklin W A, Gazdar A F, Bunn P A. Clin. Cancer Res. 2001; 7, 5-22.
3. Sirivatanauksorn V et al., Langenbecks Arch surg 1998; 383 (2): 105-115
4. Motojima K, et al., Am J Gastroenterol. 1991; 86, 1784-1788
5. Janne P A, Engelman J A, Johnson B E. J Clin Oncol 2005;23:3227-34.
6. Eberhard D A, et al. J Clin Oncol 2005;23:5900-9.
7. Le Calvez F et al., Cancer Res 2005;65:5076-83.
8. Hilbe W et al., Int J Oncol 2003;23:1121-6.
9. Shigematsu H, Gazdar A F. Int J Cancer 2006;118:257-62.
10. Kobayashi S et al., N Engl J Med 2005;352:786-92
11. Mukohara T et al., J Natl Cancer Inst 2005;97:1185-94.
12. Gone M E et al., Science 2001;293:876-80.
13. Dieterle C P et al., Clin Cancer Res 1991;10, 641-650
14. Anker P et al., Gastroenterology 1997; 112, 1114-1120
15. Dabritz J, Hanfler J, Preston R, Stieler J, Oettle H. Br J Cancer 2005;92:405-12
16. Ward R, Hawkins N et al. Am J Pathol 1998;153:373-9.
17. Orum H et al., NAR 1993; 21: 5332-533
18. Ward R et al. Am J Pathol 1998;153:373-9.
19. Kopreski M S et al., J. Nat. Canc. Inst. 2000; 92,11: 918-923.

---

The invention claimed is:

1. A method for detecting a presence or an absence of a mutant DNA sequence in a sample, the method comprising the steps of:
   a) contacting the sample with an oligonucleotide system under hybridization conditions so as to form a reaction mixture, said oligonucleotide system including a reverse primer and a mutagenic primer, wherein i) said reverse primer comprises:
      a 5' end region comprising a recognition sequence being able to be cut by a high temperature resistant restriction endonuclease; said 5' end region having covalently linked at its extremities a coupled detection system so that when the recognition sequence is cleaved by said high temperature resistant restriction endonuclease, a signal is generated;
      a 3' end region able to hybridise to a complementary region downstream of the putative mutant DNA sequence; and
   ii) said mutagenic primer comprises:
      a 5' end region comprising a first recognition sequence being able to be cut by a high temperature resistant restriction endonuclease;
      a 3' end region able to hybridise to a complementary region of the opposite extremity of the other strand of the sample DNA sequence, said mutagenic primer has a sequence so that a second recognition sequence being able to be cut by the high temperature resistant restriction endonuclease is created, only when said primer is extended on the wild type sequence so that the restriction endonuclease digests the amplicon and suppresses the amplification reaction; and said second recognition sequence being able to be cut by high temperature resistant restriction endonuclease is not polymerised when the mutant sequence is present in the DNA sample;
   b) adding with appropriate substrates and cofactors, at a suitable ionic and pH environment, both a temperature resistant DNA polymerase and said high temperature resistant restriction endonuclease to said reaction mixture under predetermined reaction conditions, such that, if the mutant DNA sequence is present in the sample, said reverse primer and said mutagenic primer hybridize to the same and prime the DNA polymerase reaction to obtain a first specific amplified product;
   c) cycling the hybridization of said oligonucleotide system so that a second specific amplified product is extended comprising the 5' end region of the reverse primer forming a double stranded recognition site for said restriction endonuclease so that the high temperature resistant restriction endonuclease cuts specifically at the recognition sequence and induces the generation of a signal by the coupled detection system; and
   d) detecting the generated signal.

2. The method for detecting the presence or the absence of a mutant DNA sequence in a sample according to claim 1 wherein the high temperature resistant restriction endonuclease is PspGI.

3. The method for detecting the presence or the absence of a mutant DNA sequence in a sample according to claim 2 wherein the mutant sequence to detect is in the human Kras gene.

4. The method for detecting the presence or the absence of a mutant DNA sequence in a sample according to claim 3 wherein the mutation of the human Kras gene sequence to detect is at codon 12, GGT of the human Kras wild type coding sequence.

5. The method for detecting the presence or the absence of a mutant DNA sequence in a sample according to claim 1 wherein the coupled detection system is a fluorophore-quencher system.

6. The method for detecting the presence or the absence of a mutant DNA sequence in a sample according to claim 5 wherein the fluorophore-quencher system has the fluorophore at the 3' end and the quencher at the 5' end of the recognition sequence.

7. The method for detecting the presence or the absence of a mutant DNA sequence in a sample according to claim 5 wherein the fluorophore-quencher system has the fluorophore at the 5' end and the quencher at the 3' end of the recognition sequence.

8. The method for detecting the presence or the absence of a mutant DNA sequence in a sample according to claim 1 wherein the 5' end region of the first and second oligonucleotide further comprises spacer regions at its 5' end.

9. An oligonucleotide system for the simultaneous selective amplification and detection of a mutant DNA sequence in a sample, including a reverse primer and a mutagenic primer, wherein:
   i) said reverse primer comprises:
      a 5' end region comprising a recognition sequence being able to be cut by a high temperature resistant restriction endonuclease; said 5' end region having covalently linked at its extremities a coupled detection system so that when the recognition sequence is cleaved by said high temperature resistant restriction endonuclease, a signal is generated;
      a 3' end region able to hybridise to a complementary region downstream of the putative mutant DNA sequence; and
   ii) said mutagenic primer comprises: a 5' end region comprising a first recognition sequence being able to be cut by a high temperature resistant restriction endonuclease;
      a 3' end region able to hybridise to a complementary region of the opposite extremity of the other strand of the sample DNA sequence, said mutagenic primer has a sequence so that a second recognition sequence being able to be cut by the high temperature resistant restriction endonuclease is created only when said primer is extended on the wild type sequence so that the restriction endonuclease digests the amplicon and suppresses the amplification reaction; and the recognition sequence being able to be cut by high temperature resistant restriction endonuclease is not polymerised when the mutant sequence is present in the DNA sample.

10. The oligonucleotide system according to claim 9 wherein the high temperature resistant restriction endonuclease is PspGI.

11. The oligonucleotide system according to claim 10 wherein the mutant sequence to detect is in the human Kras gene.

12. The oligonucleotide system according to claim 11 wherein the mutation of the human Kras gene sequence to detect is at codon 12, GGT of the human Kras wild type coding sequence.

13. The oligonucleotide system according to claim 9 wherein the coupled detection system is a fluorophore-quencher system.

14. The oligonucleotide system according to claim 13 wherein the fluorophore-quencher system has the fluorophore at the 5' end and the quencher at the 3' end of the recognition sequence.

15. The oligonucleotide system according to claim 13 wherein the fluorophore-quencher system has the fluorophore at the 3' end and the quencher at the 5' end of the recognition sequence.

16. The oligonucleotide system according to claim 13 wherein the 5' end region of the first and second oligonucleotide further comprises spacer regions at its 5' end and/or 3' end.

17. A kit for simultaneous selective amplification and detection of a mutant DNA sequence comprising the oligonucleotide system according to claim 9 and a high temperature resistant restriction endonuclease.

18. The kit according to claim 17 wherein the high temperature resistant restriction endonuclease is PspGI.

19. The kit according to claim 17 or 18 further comprising a temperature resistant DNA polymerase.

20. A method for identifying a specific mutated DNA sequence in a sample, the method comprising the steps of:
   a) contacting the sample with an oligonucleotide system under hybridization conditions so as to form a reaction mixture, said oligonucleotide system including a reverse primer and a mutagenic primer as described in claim 9 and further comprising a modified oligonucleotide having a sequence complementary to the specific mutated DNA sequence to be identified and being able to bind to said specific mutated DNA sequence with a higher binding affinity with respect to the unmodified oligonucleotide; and
   b) adding with appropriate substrates and cofactors, at a suitable ionic and pH environment, both a temperature resistant DNA polymerase and said high temperature resistant restriction endonuclease to said reaction mixture under predetermined reaction conditions, such that:
      i) if the specific mutated DNA sequence is present in the sample, said modified oligonucleotide anneals to the same and does not allow the mutagenic primer to hybridize, thus blocking an amplification reaction; and
      ii) if the specific mutated sequence is not present in the sample, said reverse primer and said mutagenic primer hybridises to the DNA sequence allowing the amplification reaction.

21. The method for identifying a specific mutated DNA sequence in a sample according to claim 20 wherein the modified oligonucleotide is a peptide nucleic acid (PNA).

22. The method for identifying a specific mutated DNA sequence in a sample according to claim 21 wherein the PNA comprises a sequence complementary to mutation of the Kras gene.

23. The method for identifying a specific mutated DNA sequence in a sample according to claim 22 wherein the PNA comprising a sequence complementary to a mutation of the Kras codon 12 gene.

24. The method for identifying a specific mutated DNA sequence in a sample according to claim 22 wherein the PNA comprises one of the following sequences: GTT, GAT or TGT.

* * * * *

SEQUENCE LISTING

<160> NUMBER OF SEQ ID NOS: 9

<210> SEQ ID NO 1
<211> LENGTH: 34
<212> TYPE: DNA
<213> ORGANISM: Artificial
<220> FEATURE:
<223> OTHER INFORMATION: synthetic primer

<400> SEQUENCE: 1
aaaccaggaa agtgtggatg acctacgggc catc              34

```
<210> SEQ ID NO 2
<211> LENGTH: 36
<212> TYPE: DNA
<213> ORGANISM: Artificial
<220> FEATURE:
<223> OTHER INFORMATION: synthetic primer

<400> SEQUENCE: 2
aaaccaggaa aggtgacacc agagaatcag aggagc                               36

<210> SEQ ID NO 3
<211> LENGTH: 38
<212> TYPE: DNA
<213> ORGANISM: Artificial
<220> FEATURE:
<223> OTHER INFORMATION: synthetic primer

<400> SEQUENCE: 3
tttcctggtt tgaatataaa cttgtggtag ttggacct                             38

<210> SEQ ID NO 4
<211> LENGTH: 38
<212> TYPE: DNA
<213> ORGANISM: Artificial
<220> FEATURE:
<223> OTHER INFORMATION: synthetic primer

<400> SEQUENCE: 4
tttcctggtt tagatttacc tctattgttg gatcatat                             38

<210> SEQ ID NO 5
<211> LENGTH: 39
<212> TYPE: DNA
<213> ORGANISM: Artificial
<220> FEATURE:
<223> OTHER INFORMATION: synthetic primer
<220> FEATURE:
<221> NAME/KEY: modified_base
<222> LOCATION: (12)..(12)

<400> SEQUENCE: 5
tttcctggtt ttagatttac ctctattgtt ggatcatat                            39

<210> SEQ ID NO 6
<211> LENGTH: 15
<212> TYPE: DNA
<213> ORGANISM: Artificial
<220> FEATURE:
<223> OTHER INFORMATION: synthetic primer

<400> SEQUENCE: 6
ggacctgttg gcgta                                                      15

<210> SEQ ID NO 7
<211> LENGTH: 15
<212> TYPE: DNA
<213> ORGANISM: Artificial
<220> FEATURE:
<223> OTHER INFORMATION: synthetic primer

<400> SEQUENCE: 7
ggacctgatg gcgta                                                      15

<210> SEQ ID NO 8
<211> LENGTH: 15
<212> TYPE: DNA
<213> ORGANISM: Artificial
```

-continued

```
<220> FEATURE:
<223> OTHER INFORMATION: synthetic primer

<400> SEQUENCE: 8
ggaccttgtg gcgta                                                           15

<210> SEQ ID NO 9
<211> LENGTH: 648
<212> TYPE: DNA
<213> ORGANISM: Homo sapiens

<400> SEQUENCE: 9
actaggaaaa ctgtaacaat aagagtggag atagctgtca gcaacttttg tgagggtgtg          60
ctacagggtg tagagcactg tgaagtctct acatgagtga agtcatgata tgatcctttg         120
agagccttta gccgccgcag aacagcagtc tggctattta gatagaacaa cttgatttta         180
agataaaaga actgtctatg tagcatttat gcattttct taagcgtcga tggaggagtt          240
tgtaaatgaa gtacagttca ttacgataca cgtctgcagt caactggaat tttcatgatt         300
gaattttgta aggtattttg aaataatttt tcatataaag gtgagtttgt attaaaaggt         360
actggtggag tatttgatag tgtattaacc ttatgtgtga catgttctaa tatagtcaca         420
ttttcattat ttttattata aggcctgctg aaaatgactg aatataaact tgtggtagtt         480
ggagctggtg gcgtaggcaa gagtgccttg acgatacagc taattcagaa tcattttgtg         540
gacgaatatg atccaacaat agaggtaaat cttgttttaa tatgcatatt actggtgcag         600
gaccattctt tgatacagat aaaggtttct ctgaccattt tcatgagt                      648
```